(12) United States Patent
Beppu et al.

(10) Patent No.: US 8,669,267 B2
(45) Date of Patent: Mar. 11, 2014

(54) PHARMACEUTICAL, FOOD OR BEVERAGE HAVING INHIBITORY ACTIVITY ON SEROTONIN TRANSPORTER

(75) Inventors: Yoshinori Beppu, Mishima-gun (JP); Nobuo Tsuruoka, Mishima-gun (JP); Hajime Komura, Mishima-gun (JP)

(73) Assignee: Suntory Holdings Limited, Osaka-shi, Osaka (JP)

( * ) Notice: Subject to any disclaimer, the term of this patent is extended or adjusted under 35 U.S.C. 154(b) by 222 days.

(21) Appl. No.: 13/059,819

(22) PCT Filed: Aug. 6, 2009

(86) PCT No.: PCT/JP2009/063934
§ 371 (c)(1),
(2), (4) Date: Feb. 18, 2011

(87) PCT Pub. No.: WO2010/021247
PCT Pub. Date: Feb. 25, 2010

(65) Prior Publication Data
US 2011/0152309 A1    Jun. 23, 2011

(30) Foreign Application Priority Data

Aug. 21, 2008 (JP) .................................. 2008-212789

(51) Int. Cl.
*A01N 43/42* (2006.01)
*A61K 31/44* (2006.01)
*C07D 471/00* (2006.01)

(52) U.S. Cl.
USPC ............................................. 514/292; 546/84

(58) Field of Classification Search
USPC ............................................. 514/292; 546/84
See application file for complete search history.

(56) References Cited

U.S. PATENT DOCUMENTS

2002/0054926 A1 *   5/2002   Williams et al. .............. 424/751

FOREIGN PATENT DOCUMENTS

EP           66518 A2   *  12/1982

OTHER PUBLICATIONS

Vaswani et. al., Progress in Neuro-Psychopharmacology & Biological Psychiatry, 2003, Elsevier, vol. 27, pp. 85-102.*
Max et. al., The New England Journal of Medicine, 1992, Massachusetts Medical Society, vol. 326, pp. 1250-1256.*
Jenike et. al., The American Journal of Psychiatry, 1990, American Psychiatric Association, vol. 147, pp. 923-928.*
Kamijima et. al., Psychiatry and Clinical Neurosciences, 2004, Wiley, vol. 58, pp. 427-433.*
Gillham et. al., Applied and Preventative Psychology, 2000, Cambridge University Press, vol. 9, pp. 63-88.*
http://www.mayoclinic.com/health/obsessive-compulsive-disorder/DS00189/DSECTION=prevention (date not provided).*
http://www.mayoclinic.com/health/panic-attacks/DS00338/DSECTION=prevention (date not provided).*
Herraiz, Journal of Agricultural Food Chemistry, 2000, American Chemical Society, vol. 48, pp. 4900-4904.*
English translation of Toshiki Morichi et al., "Biopreservation—Nyusankin ni yoru Shokuhin Biseibutsu Seigyo", Kabushiki Kaisha Saiwai Shobo, Dec. 5, 1999, pp. 10-13.
International Search Report dated Oct. 6, 2009 of PCT/JP2009/063934, filed Aug. 6, 2009.
T. Herraiz "Identification and occurrence of β-carboline alkaloids in raisins and inhibition of monoamine oxidase (MAO)", J. Agric. Food Chem., vol. 55, No. 21, pp. 8534-8540 (2007).
T. Herraiz et al. "Analysis of monoamine oxidase enzymatic activity by reversed-phase high performance liquid chromatography and inhibition by β-carboline alkaloids occurring in foods and plants", J Chromatogr. A, vol. 1120, No. 1-2, pp. 237-243 (2006).
T. Herraiz et al. "Chemical and technological factors determining tetrahydro-β-carboline-3-carboxylic acid content in fermented alcoholic beverages", J. Agric. Food Chem., vol. 41, No. 6, pp. 959-964 (1993).
T. Herraiz et al. "Identification and occurrence of tryptamine-and tryptophan-derived tetrahydro-beta-carbolines in commercial sausages," J. Agric. Food Chem., vol. 52, No. 9, pp. 2652-2658 (2004).
Toshiki morichi et al. "Biopreservation—Nyusankin ni yoru Shokuhin Biseibutsu Seigyo", Kabushiki Kaisha Saiwai Shobo, Dec. 5, 1999, pp. 10-13 (in Japanese).

* cited by examiner

*Primary Examiner* — Sarah Pihonak
(74) *Attorney, Agent, or Firm* — Drinker Biddle & Reath LLP

(57) ABSTRACT

There is provided a pharmaceutical agent, food, or beverage for treating or preventing a disease or condition that can be ameliorated by inhibiting serotonin reuptake, comprising a clinically-effective amount of (1S,3S)-1-methyl-1,2,3,4-tetrahydro-β-carboline-3-carboxylic acid.

5 Claims, 3 Drawing Sheets

☐ Group of normal mice

▨ Group administered with (1S,3S)-MTCA

■ Group of mice having depression

Reductive action of (1S,3S)-MTCA on escape-latencies in Morris water maze

Days of training (day)

- LSD test for main effect in groups
  Significance probability $p = 0.029$
- 20 mg/kg of (1S,3S)-MTCA was orally administered 1 hour before each trial — ◇ — Group of normal mice
— ● — Group administered with (1S,3S)-MTCA
— ▲ — Group of mice having depression

PHARMACEUTICAL, FOOD OR BEVERAGE HAVING INHIBITORY ACTIVITY ON SEROTONIN TRANSPORTER

CROSS REFERENCE TO RELATED APPLICATIONS

This application is the National Stage of International Application No. PCT/JP2009/063934, filed Aug. 6, 2009, and claims benefit of Japanese Application No.'s 2008-212789, filed Aug. 21, 2008, of which is herein incorporated by reference in its entirety.

TECHNICAL FIELD

The present invention relates to compositions for preventing or treating depression or complication thereof or for improving learning motivation, comprising ((1S,3S)-1-methyl-1,2,3,4-tetrahydro-β-carboline-3-carboxylic acid) as an active ingredient and having inhibitory activity on serotonin transporters.

BACKGROUND ART

Depression has been a major social problem. A survey in the United States of America estimates that the lifetime prevalence rate of depressive disorders is 26% for women and 12% for men (Non-patent Document 1). An extensive survey was also carried out in Japan, and it was reported that the lifetime prevalence rate was 14%. It was also reported that 84% of the patients with depression have complication, 61% of the patients have other mental diseases, 30% of the patients have personality disorders, and 58% of the patients have complication of physical diseases (Non-patent Document 2).

Common symptoms of depression include a wide variety of symptoms, such as depressive mood, lethargy, depressive attitudes, suicidal ideation, impatience, insomnia, anorexia, decreased sexual impulse, and physical ailments. Pathologically-severe depression is called major depression. With regard to major depression, there is reported experimental data showing that in many cases, a rapid recovery is observed during the first 40 weeks, but the recovery plateaus thereafter. It is reported that results of a 20-year follow-up survey on patients having major depression show that 15 to 19% of the patients had chronic residual symptoms such as working difficulty (Non-patent Document 3).

With regard to causes of depression, various theories are suggested. A hypothesis that was suggested in the early days and is still popular is a theory stating that a decrease in the function of monoamines in the brain is responsible for depression (this hypothesis is called "intracerebral monoamine hypothesis"). This theory is suggested on the basis of the fact that a tricyclic antidepressive agent having an action to enhance the function of monoamines in the brain by blocking the reuptake of monoamines in cells is effective for remission of depression.

Currently, especially the function of serotonin, which is an intracerebral monoamine, attracts great attention, and there is a popular hypothesis suggesting that the antidepressive action can be produced by sensitizing serotonin-1 receptors present in the serotonin nerve cell body to increase the amount of free serotonin from presynaptic cells (Non-patent Document 4). This idea is basically the same as that of the classical intracerebral monoamine hypothesis. In any cases, it is considered that depression is caused by a decrease in the intracerebral serotonin function.

With regard to medications for depression, first, a tricyclic antidepressive agent, imipramine, and monoamine oxidase inhibitors were developed about 40 years ago. On the basis of the idea that the action to increase serotonin and noradrenaline in the synaptic cleft, which is one of the features of the above drugs, is the core of the antidepressant effect, many antidepressive agents have been developed following imipramine and monoamine oxidase inhibitors. In recent years, use of selective serotonin reuptake inhibitors (SSRI) and serotonin/norepinephrine reuptake inhibitors (SNRI), which more selectively inhibit the reuptake of the monoamines by serotonin transporters, have been used in clinical practice. There are as many as 17 antidepressive agents that are approved in Japan at this time, including tricyclic/tetracyclic antidepressive agents, SSRI, and SNRI (Non-patent Document 5).

These antidepressive agents are effective against various diseases besides depression. According to package inserts of the pharmaceutical agents presented by the Pharmaceuticals and Medical Devices Agency, for example, fluvoxamine maleate, which is an SSRI, is effective against obsessive-compulsive and social anxiety disorders; paroxetine hydrochloride, which is an SSRI, is effective against panic and obsessive-compulsive disorders; and sertraline hydrochloride, which is an SSRI, is effective against a panic disorder. Further, amitriptyline hydrochloride, which is a tricyclic SNRI, is effective against nocturnal enuresis.

However, it is reported that these antidepressive agents have side effects. For example, nausea, headache, hypersensitivity and the like are reported as side effects of SSRI, and tremor, tachycardia, erection/ejaculation disorders and the like are reported as side effects of SNRI. There are several reports that side effects are increased in the case of administration of multiple antidepressive agents, compared with administration of a single antidepressive agent (Non-patent Document 6).

It is also reported that when administration of an antidepressive agent is discontinued, withdrawal symptoms may occur. Withdrawal symptoms of tricyclic/tetracyclic antidepressive agents that are reported include: digestive symptoms and physical discomfort accompanied by anxiety and irritability, such as lethargy, emesis, and headache; sleep disorders such as insomnia and multi-dream; motility disorders such as akathisia and Parkinsonian symptoms; activation of behavior that leads to a transition to a manic state; and arrhythmia. These symptoms, except for arrhythmia, are also observed in withdrawal symptoms of SSRI (Non-patent Document 7). Disturbance to the sense of equilibrium, paresthesia, aggressive/impulsive behavior and the like are reported as withdrawal symptoms characteristic of SSRI (Non-patent Document 8).

As described above, it is reported that the antidepressive agents that are widely used at this time have side effects, and the development of safe food ingredients and components, which have ever been eaten and are applicable in place of the above antidepressive agents, are expected. Royal jelly-derived compositions (Patent Document 1) and compositions comprising a hop extract as a main component (Patent Document 2) are reported as food-derived compositions having antidepressive action.

1-Methyl-1,2,3,4-tetrahydro-β-carboline-3-carboxylic acid (MTCA) is a compound contained in fruits, such as lemon, grapefruit, orange, and mandarin (Non-patent Document 9), beer, wine (Non-patent Document 10), soy sauce (Non-patent Document 11) and the like, and two types of diastereomers, (1S,3S) and (1R,3S), are known. It is known that MTCA is produced nonfermentatively in the presence of tryptophan and acetaldehyde; especially, it is known that (1S,3S)-MTCA (also called (1S,3S)-2,3,4,9-tetrahydro-1-methyl-1H-pyrido[3,4-b]-indole-3-carboxylic acid) is produced through fermentation by *S. cerevisiae* (Non-patent Document 12). Further, it is known that (1S,3S)-MTCA has antioxidation action, prevents self-polymerization reaction of γ-crystallin by the Fenton reaction using $FeCl_3$, and prevents photopolymerization reaction of γ-crystallin (Non-patent Document 13). Further, there is a description that pinoline (6-methoxy-1,2,3,4-tetrahydro-β-carboline), which is a carboline compound, inhibits the activity of monoamine oxidase A, and also inhibits the uptake of serotonin in the brain (Non-patent Document 14). Further, it is reported that pinoline reduces immobility time in forced-swimming tests using rats, and that this is the same action as that of a tricyclic antidepressive agent (Non-patent Document 15).

However, inhibitory action of serotonin uptake, antidepressive effect, and improvement of learning motivation by MTCA have completely been unknown.

RELATED ART DOCUMENTS

Patent Documents

Patent Document 1: JP 2004-131407 A
Patent Document 2: JP 2002-58450 A

Non-Patent Documents

Non-patent Document 1: APA: Am J Psychiatry 157 (Suppl 4):1-20, 2000
Non-patent Document 2: Pincus H A, et al: Arch Gen Psychiatry 56:442-449, 1999
Non-patent Document 3: Soichiro Nomura, Report of Commissioned Studies on Disaster Science, the Ministry of Health, Labour and Welfare, 2001
Non-patent Document 4: Soichi Nomura, *Bessatsu Nippon Rinsho Seishin Igaku Shokogun* I 38:236-239, 2003
Non-patent Document 5: Teruaki Tanaka et al, *Bessatsu Nippon Rinsho Seishin Igaku Shokogun* I 38:362-365, 2003
Non-patent Document 6: Shigeto Yamawaki et al, *Bessatsu Nippon Rinsho Seishin Igaku Shokogun* I 38:370-373, 2003
Non-patent Document 7: Tamam L, et al.: Adv Ther 19:17-26, 2002
Non-patent Document 8: Haddad P: J Psychopharmacol 12:305-313, 1996
Non-patent Document 9: T. Herraiz: J. Agric. Food Chem, 47 4883-4887, 1999
Non-patent Document 10: T. Herraiz: J. Agric. Food Chem, 44 3057-3065, 1996
Non-patent Document 11: Shuichi M, et al: Biosci. Biotechnol. Biochem, 69 2232-2235, 2005
Non-patent Document 12: Tomas H, et al: J. Agric. Food Chem, 41 959-964, 1993
Non-patent Document 13: Koteppa P, et al: J. Biol. Chem., 275 2455-2462, 2000
Non-patent Document 14: Pahkla R, et al: Pharmacol Toxicol, 80 122-126, 1997
Non-patent Document 15: Pahkla R, et al: Pharmacol Research, 34 73-78, 1996

SUMMARY OF INVENTION

Technical Problem

Conventionally, it has been difficult to obtain an agent for preventing or treating depression or complication thereof and an agent for improving learning motivation that produce effects thereof while achieve few side effects and high safety. Furthermore, there has been a problem that synthesis of pharmaceutical agents requires a multi-step process and is, thus, costly. Thus, there are strong demands for antidepressant substances and learning motivation improving substances that can be obtained from a food-derived substance through a simple process. An object of the present invention is to provide pharmaceutical agents or foods for preventing or treating depression or complication thereof or for improving learning motivation that are effective and highly safe.

Solution to Problem

The present inventors conducted intensive and extensive studies in an attempt to solve the above problems, and isolated and identified (1S,3S)-MTCA from a culture supernatant of lactic acid bacteria. Thereafter, they found that (1S,3S)-MTCA had inhibitory activity on serotonin transporters, which is an indicator of antidepressant effect in vitro.

To evaluate the antidepressant effect of (1S,3S)-MTCA, mice in a condition in which motivation was decreased through open-space swimming were prepared, and the mice were used for determining the reducing effect on the time taken to reach an escape platform (the time is also referred to as "escape-latency") in Morris water maze tests when (1S,3S)-MTCA was administered to the mice, and thereby antidepressant effect of (1S,3S)-MTCA is judged. From the results it was confirmed that (1S,3S)-MTCA had the effect of reducing the time taken to reach the escape platform and had the antidepressant effect. Further, since the time taken to reach an escape platform in Morris water maze tests is decreased by learning based on space perception, it can also be considered that the effect of reducing the time taken to reach the escape platform in the present invention is the effect of improving learning motivation decreased through the open-space swimming, and it was confirmed that (1S,3S)-MTCA also had the effect of improving learning motivation.

Specifically, the present invention is:

1. A pharmaceutical agent, food, or beverage for treating or preventing a disease or condition that can be ameliorated by inhibiting serotonin reuptake, comprising a clinically-effective amount of (1S,3S)-1-methyl-1,2,3,4-tetrahydro-β-carboline-3-carboxylic acid;

2. A pharmaceutical agent, food, or beverage for treating or preventing a disease or condition that can be ameliorated by inhibiting serotonin reuptake, comprising a microorganism having a capability of producing (1S,3S)-1-methyl-1,2,3,4-tetrahydro-β-carboline-3-carboxylic acid or a processed product of the microorganism;

3. A pharmaceutical agent, food, or beverage for treating or preventing a disease or condition that can be ameliorated by inhibiting serotonin reuptake, comprising a culture supernatant of a microorganism having a capability of producing (1S,3S)-1-methyl-1,2,3,4-tetrahydro-β-carboline-3-carboxylic acid or a processed product of the culture supernatant;

4. The pharmaceutical agent, food, or beverage according to any one of 1 to 3, further comprising an additive acceptable as a pharmaceutical agent or food;

5. The pharmaceutical agent, food, or beverage according to 2 or 3, wherein the microorganism is a lactic acid bacterium;

6. The pharmaceutical agent, food, or beverage according to 5, wherein the lactic acid bacterium belongs to *Streptococcus, Lactobacillus, Leuconostoc, Pediococcus, Bifidobacterium, Tetragenococcus, Weissella, Enterococcus, Melisso-* coccus, Lactococcus, Carnobacterium, Vagococcus, Atopobium, Lactosphaera, Oenococcus, Abiotrophia, Paralactobacillus, Granulicatella, Atopobactor, Alkalibacterium, or Olsenella;

7. The pharmaceutical agent, food, or beverage according to 2 or 3, wherein the microorganism belongs to *Lactobacillus plantarum* or *Lactobacillus brevis*;

8. The pharmaceutical agent, food, or beverage according to any one of 1 to 3, wherein the disease or condition that can be ameliorated by inhibiting serotonin reuptake is depression;

9. The pharmaceutical agent, food, or beverage according to any one of 1 to 3, wherein the disease or condition that can be ameliorated by inhibiting serotonin reuptake is complication of depression;

10. The pharmaceutical agent, food, or beverage according to any one of claims 1 to 3, wherein the disease or condition that can be ameliorated by inhibiting serotonin reuptake is decreased learning motivation;

11. A method for producing the pharmaceutical agent, food, or beverage according to any one of 1 to 3, comprising the step of culturing in a medium a microorganism having a capability of producing (1S,3S)-1-methyl-1,2,3,4-tetrahydro-β-carboline-3-carboxylic acid;

12. A serotonin reuptake inhibitor, comprising (1S,3S)-1-methyl-1,2,3,4-tetrahydro-β-carboline-3-carboxylic acid.

Advantageous Effect of Invention

The present invention provides a pharmaceutical agent, food, or beverage having the antidepressant effect and the learning motivation-improving effect. It is known that (1S,3S)-MTCA used as an active ingredient in the pharmaceutical agent, food, or beverage of the present invention is present in foods. Thus, it is considered that (1S,3S)-MTCA is significantly safe and less concern about side effects and the like, compared with other compounds having the similar activity, e.g., pinoline (6-methoxy-1,2,3,4-tetrahydro-β-carboline), which is an intracerebral substance described in Non-patent Document 14. Furthermore, the pharmaceutical agent, food, or beverage of the present invention has an advantage that they can be produced easily.

DESCRIPTION OF EMBODIMENT

Figure 1:
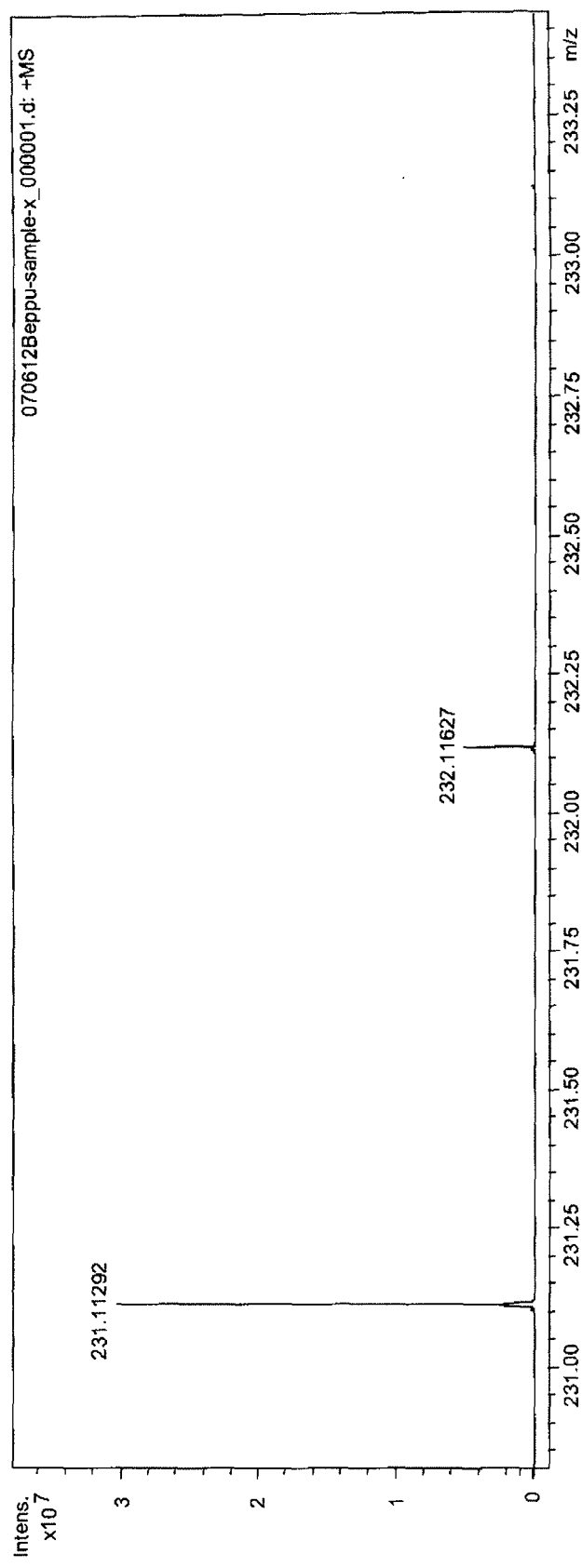
FIG. 1 is results of mass spectrometry of fractions (Develosil C-30 fractions) obtained from a culture supernatant of lactic acid bacteria.

A pharmaceutical agent, food, or beverage of the present invention comprises (1S,3S)-MTCA as an active ingredient. (1S,3S)-MTCA used in the present invention is a compound represented by the following formula:

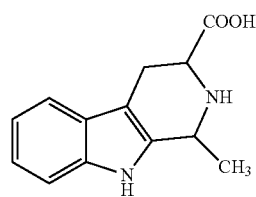

[Formula 1]

The pharmaceutical agent, food, or beverage comprising (1S,3S)-MTCA (in this specification, the pharmaceutical agent, food, or beverage is sometimes referred to simply as "composition") has inhibitory activity on serotonin transporters and is effective for the treatment of depression or complication thereof, the improvement of learning motivation, the treatment of obsessive-compulsive disorder, social anxiety disorder, panic disorder, and nocturnal enuresis, and the like.

Either of synthesized (1S,3S)-MTCA and (1S,3S)-MTCA that is commercially available as a reagent may be used. As a reagent, for example, (1S,3S)-2,3,4,9-tetrahydro-1-methyl-1H-pyrido[3,4-b]-indole-3-carboxylic acid is commercially available from Wako Pure Chemical Industries, Ltd. Further, (1S,3S)-MTCA extracted from culture supernatants of lactic acid bacteria, fruits such as lemon, grapefruit, orange, and mandarin, or food ingredients such as beer, wine, and soy sauce may be used.

In the production of a food comprising a high level of (1S,3S)-MTCA, (1S,3S)-MTCA may be produced in the food or added externally to the food. In the case of producing (1S,3S)-MTCA in a food, tryptophan and acetaldehyde are added to the food and the mixture is stood still for several days and, in some cases, heated to about 80° C., whereby (1S,3S)-MTCA can be produced nonfermentatively in the food. Alternatively, (1S,3S)-MTCA can also be produced through fermentation as described below.

As described in the Examples below, the present inventors also found that (1S,3S)-MTCA was contained in a supernatant in media in which lactic acid bacteria (*Lactobacillus plantarum* SAM 2446 strain (FERM BP-10438)) had been cultured.

In the fractionation of (1S,3S)-MTCA from the above food ingredient, culture supernatant or the like, the food ingredient, the culture supernatant or the like may be subjected to fractionation procedure directly, or (1S,3S)-MTCA in the ingredient may be concentrated by freeze-drying, liquid-liquid distribution extraction using an organic solvent, or the like prior to the fractionation procedure. Any method can be used to carry out the fractionation procedure; for example, after rough fractionation by ultrafiltration treatment or the like, fractionation can be carried out using a reverse phase column or the like. The liquid-liquid distribution extraction, ultrafiltration treatment, and reverse phase column treatment can be carried out by methods that are commonly used by a person skilled in the art.

The fact that (1S,3S)-MTCA is obtained by the above method can be confirmed by, for example, measuring MS or NMR spectra.

(1S,3S)-MTCA contained in the composition of the present invention may be used in the form of a pharmaceutically-acceptable salt, such as hydrochloride, or in the form of a salt (prodrug) that is converted into (1S,3S)-MTCA in the body. Further, a racemic body of (1S,3S)-MTCA may also be used as (1S,3S)-MTCA in the composition.

The present invention also provides the pharmaceutical composition, food, or beverage comprising a microorganism having the capability of producing (1S,3S)-MTCA or a processed product thereof or a culture supernatant of the microorganism or a processed product thereof.

As used herein, the term "a microorganism having the capability of producing (1S,3S)-MTCA" refers to a microorganism that produces (1S,3S)-MTCA when cultured in effective conditions. The effective conditions can appropriately be determined by a person skilled in the art. The microorganism's capability of producing (1S,3S)-MTCA can be confirmed by detection of (1S,3S)-MTCA and the like in the analysis of the microorganism (including the microorganism, dried product of the microorganism, culture medium of the microorganism, extract of the microorganism and the like) by using a common method, for example, liquid chromatography (LC), mass spectrometry (MS), nuclear magnetic resonance (NMR) or the like. The microorganisms having such capability of producing include a microorganism that acquires the capability of producing (1S,3S)-MTCA when culture conditions (e.g., medium composition, temperature conditions in the culture, pH conditions in the culture, culture density) are appropriately adjusted.

The microorganism may be a microorganism obtained from nature, or may be a variant and/or recombinant designed to have the capability of producing (1S,3S)-MTCA. Such variant and/or recombinant include those that are designed such that the capability of producing (1S,3S)-MTCA is higher than that of wild type when they are cultured in media having the same composition.

Such a microorganism having the capability of producing (1S,3S)-MTCA may be a lactic acid bacterium, yeast, *Bacillus subtilis* or the like. Examples of lactic acid bacteria include microorganisms belonging to *Streptococcus, Lactobacillus, Leuconostoc, Pediococcus, Bifidobacterium, Tetragenococcus, Weissella, Enterococcus, Melissococcus, Lactococcus, Carnobacterium, Vagococcus, Atopobium, Lactosphaera, Oenococcus, Abiotrophia, Paralactobacillus, Granulicatella, Atopobactor, Alkalibacterium,* or *Olsenella*. Examples of yeasts include microorganisms belonging to *Candida* or *Saccharomyces*. Examples of *Bacillus subtilis* include *Bacillus subtilis* (*B. subtilis*).

Especially preferred microorganism are lactic acid bacteria belonging to *Lactobacillus plantarum* (more specifically, *Lactobacillus plantarum* SAM 2446 strain (FERM BP-10438)) and *Lactobacillus brevis* (more specifically, *Lactobacillus brevis* SAM 2447 strain (FERM BP-10439)).

*Lactobacillus plantarum* SAM 2446 and *Lactobacillus brevis* SAM 2447 strains were accepted for international deposit on Oct. 26, 2005 by the International Patent Organism Depositary, the National Institute of Advanced Industrial Science and Technology (Central 6, 1-1-1 Higashi, Tsukuba, Ibaraki, Japan), and deposit numbers FERMBP-10438 and FERMBP-10439 were given to the strains, respectively. Mycological properties of the *Lactobacillus plantarum* SAM 2446 strain (FERM BP-10438) are shown in Table 1, and those of the *Lactobacillus brevis* SAM 2447 strain (FERM BP-10439) are shown in Table 2.

TABLE 1

| *Lactobacillus plantarum* SAM 2446 strain (FERM BP-10438) | |
|---|---|
| Form of cells | Bacillus |
| Spore | Not formed |
| Gram stain | Positive |
| Motility | None |
| Spore | None |
| Catalase reaction | Negative |
| Growth at 15° C. | Good |

TABLE 1-continued

| *Lactobacillus plantarum* SAM 2446 strain (FERM BP-10438) | |
|---|---|
| Growth at 45° C. | No growth |
| Assimilation property of sugar | |
| Glycerol | − |
| D-arabinose | − |
| L-arabinose | + |
| Ribose | + |
| D-xylose | − |
| L-xylose | − |
| Galactose | + |
| Glucose | + |
| Fructose | + |
| Mannose | + |
| Rhamnose | − |
| Mannitol | + |
| Sorbitol | + |
| α-methyl-D-mannoside | − |
| α-methyl-D-glucoside | − |
| Cellobiose | + |
| Lactose | + |
| Melibiose | − |
| Trehalose | − |
| Raffinose | − |
| Xylitol | − |

(Positive: +, Negative: −, Weakly-positive: w)

TABLE 2

| *Lactobacillus brevis* SAM 2447 strain (FERM BP-10439) | |
|---|---|
| Form of cells | Bacillus |
| Spore | Not formed |
| Gram stain | Positive |
| Motility | None |
| Spore | None |
| Catalase reaction | Negative |
| Growth at 15° C. | Good |
| Growth at 45° C. | No growth |
| Assimilation property of sugar | |
| Glycerol | − |
| D-arabinose | w |
| L-arabinose | + |
| Ribose | + |
| D-xylose | − |
| L-xylose | − |
| Galactose | + |
| Glucose | + |
| Fructose | + |
| Mannose | − |
| Rhamnose | − |
| Mannitol | w |
| Sorbitol | − |
| α-methyl-D-mannoside | − |
| α-methyl-D-glucoside | w |
| Cellobiose | − |
| Lactose | − |
| Melibiose | − |
| Trehalose | − |
| Raffinose | − |
| Xylitol | − |

(Positive: +, Negative: −, Weakly-positive: w)

The present invention also provides a method for producing a pharmaceutical agent, food, or beverage, comprising the step of culturing in a medium a microorganism having the capability of producing (1S,3S)-MTCA. The culture of the microorganism can be carried out by inoculating the microorganism in an appropriate medium to culture the microorganism using a publicly-known method, which is appropriate to the type of the microorganism.

An example in which a lactic acid bacterium is cultured as the microorganism is described below. As a medium, for example, an agar medium and/or liquid medium can be used.

To the medium, a carbon source and a nitrogen source are added at desired concentrations and, when necessary, trace nutrients such as inorganic ions and vitamins are added. More simply, for example, a commercially-available medium such as an MRS medium may be used and, when necessary, an additive may be added to the medium for use. After the medium is prepared, pH of the medium is adjusted to a range of pH 6.0 to 7.0 by using an appropriate acid or base, and the medium can be sterilized by using an autoclave and the like.

To increase production of (1S,3S)-MTCA, for example, appropriate amounts of tryptophan and acetaldehyde may be added to the medium.

Thereafter, a lactic acid bacterium is inoculated in the medium to culture at a culture temperature of 10° C. to 45° C. for normally 1 to 2 days by shaking, or static, if necessary, in a tank or the like for industrial production, thereby allowing the microorganism to grow in the medium. Culture conditions may be varied, depending on the microorganism used; for example, when *Lactobacillus plantarum* is used, the microorganism can be cultured by static culture at about 37° C. for 1 day using an MRS medium with a pH of about 6.5. The microorganism thus cultured may be subjected to centrifugal separation, when desired, and thereafter to filtration, when necessary, whereby a culture supernatant can be obtained.

As apparent from the Examples below, (1S,3S)-MTCA has inhibitory activity on serotonin transporters, and also has the antidepressant effect and the learning motivation-improving effect. As used herein, the treatment of a disease or condition includes prevention of progression of the disease or condition, amelioration of the disease or condition, and prevention of the disease or condition.

The composition of the present invention comprises a clinically-effective amount of (1S,3S)-MTCA. The term "clinically-effective amount" refers to a clinically-effective amount sufficient to produce the antidepressant effect, the learning motivation-improving effect and the like. There is no particular upper limit to the amount of (1S,3S)-MTCA to be administered but in economical point of view, generally, the amount is preferably not greater than 100 mg/kg.

In order for the composition of the present invention to adequately produce its effects, it is preferred that the composition comprises (1S,3S)-MTCA in an amount of 1 μg/kg to 100 mg/kg (preferably 2 μg/kg to 50 mg/kg, more preferably 4 μg/kg to 25 mg/kg) per dose; more specifically, when a human adult is the subject, the composition comprises (1S,3S)-MTCA in an amount of 60 μg to 6000 mg (preferably 120 μg to 3000 mg, more preferably 240 μg to 1500 mg) per dose.

An ingredient such as a food ingredient comprising (1S,3S)-MTCA, a microorganism having the capability of producing (1S,3S)-MTCA, a culture supernatant of the microorganism, a culture product comprising the microorganism or the like may be contained in the composition of the present invention, or the ingredient, the microorganism, the culture supernatant, the culture product or the like may be subjected to extraction and fractionation procedure to isolate or purify (1S,3S)-MTCA and this isolated or purified (1S,3S)-MTCA may be contained in the composition of the present invention. Alternatively, they may be subjected to normal sterilization treatment and used, or may be processed into a concentrate, dry powder or the like by concentrating under reduced pressure, freeze-drying, or the like and the processed product may be contained. In the processing into a dry powder, a commonly-used diluting agent such as dextrin, macromolecular starch hydrolysate, or macromolecular peptide may be used to process into a dry powder. In view of workability and storage stability, it is preferred that the composition of the present invention is processed into a powder.

The composition of the present invention may be in the form of a food or beverage (including foods, beverages, seasonings, alcoholic beverages, functional foods and the like), or a pharmaceutical agent, depending on the purpose of use.

Examples of foods and beverages suitable for the present invention include various foods and beverages such as candy, troche, gum, yogurt, ice cream, pudding, jelly, soft adzuki-bean jelly, alcoholic beverage, coffee beverage, juice, fruit juice beverage, carbonated beverage, soft drink, milk, whey beverage, and lactic acid bacteria beverages. These foods and beverages can be produced by a method commonly used.

When necessary, various additives may be added to the above foods and beverages. Specifically, an additive that is commonly used as a food ingredient can be added by a method commonly used; examples include glucose, fructose, sucrose, maltose, sorbitol, stevioside, rubusoside, corn syrup, lactose, citric acid, tartaric acid, malic acid, succinic acid, lactic acid, L-ascorbic acid, dl-alpha-tocophenol, sodium erythorbate, glycerin, propylene glycol, glycerine fatty acid ester, polyglycerine fatty acid ester, sucrose fatty acid ester, sorbitan fatty acid ester, propylene glycol fatty acid ester, gum arabic, carrageenan, casein, gelatin, pectin, agar, vitamin B family, nicotinic acid amide, calcium pantothenate, amino acids, calcium salts, pigments, flavorings, and preservatives.

In the preparation of the pharmaceutical agent of the present invention, various additives may be added as necessary, and the pharmaceutical agent may be prepared in various dosage forms by a method commonly used. For example, the pharmaceutical agent of the present invention may be in the form of an oral pharmaceutical agent, such as a tablet, capsule, granule, powder, syrup, and extract, or a parenteral pharmaceutical agent, such as ointment, eye ointment, lotion, cream, patch, suppository, instillation, nasal drop, and injection. The additive to be used is not particularly limited, and any additive, which is commonly used, can be used. For example, a solid support, such as starch, lactose, sucrose, mannitol, carboxymethyl cellulose, cornstarch, and an inorganic salt; a liquid support, such as distilled water, physiological saline, an aqueous solution of glucose, an alcohol such as ethanol, propylene glycol, and polyethylene glycol; an oil-based carrier, such as various animal and vegetable oils, white petrolatum, paraffin, and waxes, and the like can be used.

The composition of the present invention may further contain, in addition to (1S,3S)-MTCA, which is an active ingredient, another active ingredient that is known to have antidepressant effect, as desired. Such another active ingredient is required to be safe when used in combination with (1S,3S)-MTCA.

For example, substances that are publicly known in the art, such as an antidepressive agent such as SSRI and SNRI, an anti-anxiety agent, and St. John's wort, may be contained either alone or in combination in the composition of the present invention.

When the composition of the present invention comprises a microorganism having the capability of producing (1S,3S)-MTCA or a processed product thereof, or a culture supernatant or a processed product thereof, a substance derived from the microorganism and known to have the antidepressant effect and the like may be contained.

The pharmaceutical agent, food, or beverage of the present invention may indicate a specific intended purpose of use (e.g., anti-depression, prevention of complication of depression, improvement of learning motivation, health maintenance) and/or specific usage (e.g., amount, number, and method of intake) on a package thereof or the like.

The present invention is described in detail by the following Examples. However, it is understood that the scope of the present invention is not limited by the Examples.

In the Examples below, the inhibitory activity of (1S,3S)-MTCA on serotonin transporters was determined. Further, effects of (1S,3S)-MTCA on the antidepressant and the improvement of learning motivation were determined by using mice. Furthermore, a pharmaceutical agent, food, and beverage comprising (1S,3S)-MTCA were produced.

EXAMPLE 1

Isolation and Identification of (1S,3S)-MTCA in a Culture Supernatant of Lactic Acid Bacteria (1) Culture of Lactic Acid Bacteria Fifty five grams of a commercially-available MRS medium (manufactured by Difco) was dissolved in 1 L of water, and the pH was adjusted to pH 6.5 with 1 N hydrochloric acid or 1 N sodium hydroxide solution, followed by autoclave sterilization. Then, lactic acid bacteria (*Lactobacillus plantarum* SAM 2446 strain (FERM ABP-10438)) was inoculated in the medium and cultured by static at a culture temperature of 37° C. for 1 day. The resulting culture product was subjected to centrifugal separation at 8000 rpm for 5 minutes, and the resulting centrifugal supernatant was passed through a filter having a pore size of 0.45 μm to obtain 1 L of culture supernatant.

(2) Ultrafiltration of Culture Supernatant of Lactic Acid Bacteria

Two hundreds and thirty five milliliters of the culture supernatant thus obtained was passed through an ultrafiltration membrane (10000 molecular weight cutoff, Amicon-YM10, manufactured by Millipore), and the fraction that had passed through the membrane was obtained as an ultrafiltration fraction (165 mL).

(3) Confirmation of Peak of (1S,3S)-MTCA by Using Chromatography Equipped with Develosil C-30-UG-5

The fact that (1S,3S)-MTCA was contained in the ultrafiltration fraction was confirmed by using a column for analysis, Develosil C-30-UG-5 (150 mm×4.6 mm) (manufactured by Nomura Chemical Co., Ltd.) under the following measurement conditions. As mobile phases, the following two solutions were used: distilled water containing 0.1% formic acid (Buf. A); and a solution of 80% acetonitrile and 20% distilled water containing 0.1% formic acid (Buf. B). The flow rate of the mobile phases was set to 1 mL/min., and elution was conducted using the following gradient conditions: isocratic elution for 8.3 minutes with 10% Buf. B/90% Buf. A; linear gradient elution for 19.92 minutes from 10% Buf. B/90% Buf. A to 16% Buf. B/84% Buf. A; linear gradient elution for 1.66 minutes from 16% Buf. B/84% Buf. A to 100% Buf. B; and isocratic elution for 4.98 minutes with 100% Buf. B. The ultrafiltration fraction was diluted at two-fold with Buf. A and 200 μL of the diluted fraction was injected. The detection was set to 215 nm. A peak corresponding to (1S,3S)-MTCA was detected at a retention time of around 17 minutes.

(4) Crude Purification Using CHP20P (Manufactured by Mitsubishi Chemical Corporation) Chromatography The ultrafiltration fraction (165 mL) obtained in (2) was charged onto a column CHP20P (500 mL) manufactured by Mitsubishi Chemical Corporation that had been equilibrated in advance with 2.5 L of Buf. A, and eluted at a flow rate of 300 mL/hour by using sequentially 750 mL of Buf. A, 500 mL of 10% Buf. B/90% Buf. A, and 500 mL of 20% Buf. B/80% Buf. A. At the time of the elution with 20% Buf. B/80% Buf. A, eluent was fractionated in 50 mL for each. When the fractions thus obtained were analyzed in accordance with the method of (3), a peak of (1S,3S)-MTCA was detected in the fifth to seventh fractions. Thus, the fifth to seventh fractions were recovered as the fraction comprising (1S,3S)-MTCA and named CHP20P fraction. The CHP20P fraction thus obtained had a volume of 150 mL, and the weight after the freeze-drying was 133 mg.

(5) Purification, Fractionation, and Identification Using Develosil C-30-UG-5 Chromatography As a sample to be analyzed, 2000 μL of a mixture obtained by dissolving 10 mg of a freeze-dried product of the CHP20P fraction obtained in (4) in Buf. A was used. As a column for the analysis, Develosil C-30-UG-5 (200 mm×20 mm) (manufactured by Nomura Chemical Co., Ltd.) was used. The flow rate was set to 2.5 mL/min., and elution was conducted using the following gradient conditions: isocratic elution for 42.48 minutes with 5% Buf. B/95% Buf. A; linear gradient elution for 127.44 minutes from 5% Buf. B/95% Buf. A to with 30% Buf. B/70% Buf. A; and isocratic elution for 42.48 minutes with 100% Buf. B. The detection was set to 215 nm. A peak detected at a retention time of around 84 to 90 minutes was named Develosil C-30 fraction. This operation was repeated 10 times, and 3.4 mg of Develosil C-30 fraction was obtained from a total of 100 mg of CHP20P fraction. When the Develosil C-30 fraction thus obtained was analyzed in accordance with (3), and a peak corresponding to (1S,3S)-MTCA was confirmed. Thereafter, this Develosil C-30 fraction as a sample for structural analysis was subjected to NMR and MS analysis, and it was confirmed that (1S,3S)-MTCA was contained. The result of MS analysis of Develosil C-30 fraction is shown in FIG. 1.

EXAMPLE 2

Confirmation of the Inhibitory Effect of (1S,3S)-MTCA on Serotonin Transporters

A commercially-available (1S,3S)-2,3,4,9-tetrahydro-1-methyl-1H-pyrido[3,4-b]-indole-3-carboxylic acid reagent (manufactured by Wako Pure Chemical Industries, Ltd.) was used as a subject substance ((1S,3S)-MTCA), and the inhibitory effect of (1S,3S)-MTCA on serotonin transporters was determined using a method described in Masahiko T, et al: European Journal of Pharmacology 368 277-283, 1999.

(1) Preparation of Cell Homogenate

CHO cells were transfected with a secretory vector pRc/CMV, in which cDNA of a human serotonin transporter was incorporated, by a calcium phosphate method. Thereafter, the CHO cells were cultured in 17.5 ml of Dulbecco's Modified Eagles' Medium (manufactured by Mediatech) (comprising 0.1 mM Non-Essential Amino Acid Solution For MEM (manufactured by Mediatech), 5% (V/V) Fetal Clone Bovine serum product (manufactured by Hyclone Laboratories), and 1 U/μL of penicillin/streptomycin solution (manufactured by Mediatech)) in a 150-mm Petri dish. The culture was carried out in an environment of 10% $CO_2$ and 90% air at a temperature of 37° C. and a humidity of 100%.

Then, the medium was removed by aspiration to prepare a cell homogenate. After the cells were washed with 4 mL of modified Puck's D1 solution (solution 1), solution 1 and 10 mL of 100 mM EGTA (ethylene glycol-bis(β-aminoethyl ether)N,N,N',N'-tetraacetic acid) were added, followed by incubation at 37° C. for 5 minutes. Thereafter, the cells were separated and recovered with a rubber spatula, moved into a centrifuge tube, and centrifuged at 4° C. for 5 minutes at 110×g. The resulting pellet was suspended in a solution (solution 2) comprising 50 mM Tris-HCl (pH 7.4), 120 mM NaCl, 5 mM KCl, and 0.1% BSA, and homogenized for 10 seconds by a Polytron (manufactured by Brinkmann Instruments) at setting 6. The resulting homogenate was centrifuged at 4° C. for 10 minutes at 35600×g. The resulting pellet was suspended in the solution 2 of the equal volume and centrifuged again at 4° C. for 10 minutes at 35600×g. The centrifugal supernatant was removed, and the resulting pellet was suspended in the solution 2 to form a cell homogenate. The cell homogenate was stored at −80° C. until the assay. The concentration of protein in the resulting cell homogenate was measured by a Lowry method using bovine serum albumin (BSA) as a standard.

(2) Assay

Thereafter, 25 µL, of (1S,3S)-MTCA solution dissolved in physiological saline (100 µg/mL) and the solution 2 (225 µL) comprising 2 nM [$^3$H] imipramine were added to a 96-hole microplate, and the cell homogenate (amount of protein: 15 µg) obtained in (1) was added to the microplate, followed by incubation at 22° C. for 60 minutes. Note that imipramine used in this assay is a tricyclic antidepressive agent known to have the effect of inhibiting the reuptake of serotonin by a serotonin transporter by binding to the serotonin transporter. As a control, the cell homogenate comprising no (1S,3S)-MTCA was incubated likewise. Non-specific binding of [$^3$H] imipramine to the cell homogenate was determined using 10 µM imipramine.

After the incubation was completed, the sample was expeditiously filtered using a 96-hole cell harvester (Unifilter, manufactured by Packard) with a built-in glass fiber filter (GF/G, manufactured by Packard) impregnated in advance with 0.3% PEI, and thereafter the sample was washed several times with ice-cooled 50 mM Tris-HCl (pH 7.4) and 150 mM NaCl to remove [$^3$H] imipramine that did not bind. The glass fiber filter after the washing was dried. Then, a scintillation cocktail (Microscint O, manufactured by Packard) was added, and radioactivity of the sample was measured by a scintillation counter (Topcount, manufactured by Packard), whereby the amount of [$^3$H] imipramine bound to the cell homogenate was measured.

In this assay, it was found that when the amount of [$^3$H] imipramine that specifically bound to the cell homogenate in the control was 100, the amount of [$^3$H] imipramine that specifically bound to the cell homogenate in 100 µg/mL of the (1S,3S)-MTCA sample was only 69. This result suggests that (1S,3S)-MTCA competitively inhibits binding of imipramine to a serotonin transporter and, therefore, suggests that (1S,3S)-MTCA, like imipramine, binds to a serotonin transporter. If it is true that (1S,3S)-MTCA binds to a serotonin transporter, it is inferred that (1S,3S)-MTCA also has the same inhibitory action on serotonin transporters action (i.e., serotonin reuptake inhibitory action) as that of imipramine.

EXAMPLE 3

Evaluation of Effects of (1S,3S)-MTCA on the Antidepressant and the Improvement of Learning Motivation by Behavioral Scientific Pharmacological Tests Using Mice Subject The subjects were 90 male C57BL/6N mice that had never been subjected to any experiment. At the beginning of the experiment, an average age of the subjects was about 12 weeks old, and an average weight of the subjects was 24.9 g (SD=3.30). The subjects were housed in an acrylic cage in an animal house in which the room temperature was 23° C. and the humidity was 50 to 60%. The inside of the animal house was set such that a light is alternately turned on and off in a 12-hour cycle (light period: from 8:00 AM to 8:00 PM). This experiment was carried out every day at the same time period during the light period. As feedstuff, a dry solid feed (Labo MR manufactured by Nosan Corporation) was fed. The supply of neither feedstuff nor water was limited.

The subjects were divided into 3 groups, and they were named noOS-Vehicle group (group of normal mice) (n=10), OS-(1S,3S)-MTCA-administered group (n=10), and OS-Vehicle group (group of mice having depression) (n=10), respectively.

Experimental Device

A circular pool with an inner diameter of 95 cm and a depth of 35 cm was used. The pool was surrounded by white partitions each having a height of 120 cm and a width of 150 cm. An escape platform was constituted of a circular plate with a diameter of 11.5 cm and a thickness of 0.5 cm and a pedestal on which the circular plate was mounted, and the escape platform had a height of 21 cm. The escape platform was placed in the pool only in Phase 2 described below. The place where the escape platform was located was a central part of one of the four evenly-divided fan-shaped quadrants (Quadrant 1 to 4) of a circular water surface, and was determined for each subject. The water level was at about 0.5 cm above the surface of the escape platform. The shortest distance between an edge of the escape platform and an inner wall of the pool was set to 20 cm. The water was made opaque with titanium oxide, and the water temperature was maintained at 24±1° C. Stimuli outside the device that the subjects could use as cues for memorizing the location of the escape platform were removed as completely as possible from areas around the pool. At the time of the experiment, light was applied with a fluorescent lamp from the outside of the area where the experiment device was placed, and the illuminance on the water surface was about 240 lux.

EXPERIMENT

Phase 1: Open-Space Swimming Treatment Phase (Day 1 to 5)

All subjects of the two groups excluding the noOS-Vehicle group were subjected to the open-space swimming treatment (OS) five minutes a day for five consecutive days. The subjects were placed into the pool through a pool-side and allowed to swim freely. The swimming subjects were recorded by a video camera provided at a place that was about 2 m from the water surface of the pool, and the time spent in each imaginary quadrant (Quadrant 1 to 4) formed on the water surface of the pool and the swim distance were analyzed using a video tracking system for follow-up of behaviors and analysis.

Phase 2: Water Maze Learning Training Phase (Day 6 to 15)

To the subjects of the group administered with OS-(1S,3S)-MTCA, 20 mg of (1S,3S)-2,3,4,9-tetrahydro-1-methyl-1H-pyrido[3,4-b]-indole-3-carboxylic acid (manufactured by Wako Pure Chemical Industries, Ltd.) ((1S,3S)-MTCA) per kilogram of the weight was orally administered in the form of 10 mL aqueous solution every day 60 minutes before the water maze learning training, using a Teflon (registered trademark) feeding tube (gauge 1.2 mm, length 38 mm) equipped with a silicon ball (diameter: 2 mm) at a tip of the feeding tube. In the preparation of the aqueous solution of (1S,3S)-MTCA, distilled water was used. To the subjects of the noOS-Vehicle group and the OS-Vehicle group, distilled water was administered by the same method. In each trial, the subject was placed into the pool from a pool-side of one of the four imaginary quadrants (Quadrant 1 to 4) of the pool, in a random order, with its head facing the pool-side, and the time elapsed before both forefeet touched the escape platform was measured as the time taken to reach the escape platform (the time is also referred to as "escape-latency"). When the subject climbed onto the escape platform, the subject was allowed to stay there for 10 seconds and then placed into the pool again by the same process. This trial was repeated five times a day. When the subject did not reach the escape platform within 60 seconds after it was placed into the pool, the experimenter guided the subject onto the escape platform, allowed the subject to stay there for 10 seconds, and then repeated the trial. In this case, the escape-latency was recorded as 60 seconds and defined as a failure trial. An interval between trials was set to 30 seconds. The water maze learning training was carried out for 10 consecutive days.

Results

Figure 2:
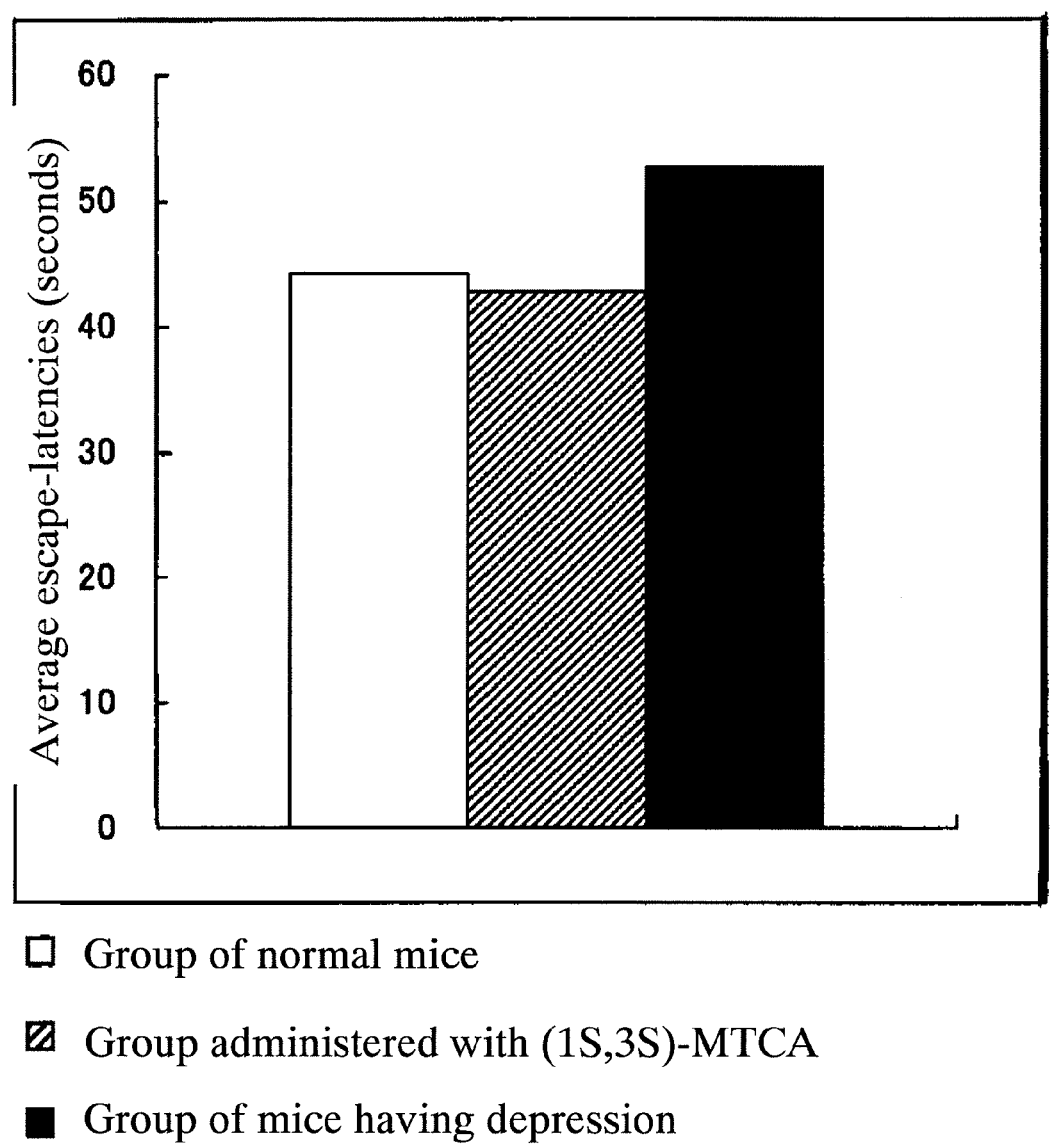
FIG. 2 is the antidepressant effect and the learning motivation-improving effect of single administration of (1S,3S)-MTCA in a behavioral scientific pharmacological test using a combination of open-space swimming and Morris water maze tests.

Average escape-latencies (seconds, average of five trials) of the noOS-Vehicle group (group of normal mice), the OS-(1S,3S)-MTCA-administered group, and the OS-Vehicle group (group of mice having depression) in Day 1 are shown in FIG. 2. While the average escape-latency of the OS-Vehicle group (group of mice having depression) was 52.6 seconds, the average escape-latency of the OS-(1S,3S)-MTCA-administered group was 42.7 seconds. The average escape-latency of the noOS-Vehicle group (group of normal mice) was 44.1 seconds (FIG. 2). The foregoing results show that the time taken to reach the escape platform was decreased from Day 1 of administration in the OS-(1S,3S)-MTCA-administered group, compared with the OS-Vehicle group (group of mice having depression). From the results, the antidepressant action and the learning motivation-improving action of the single administration of (1S,3S)-MTCA were confirmed.

Figure 3:
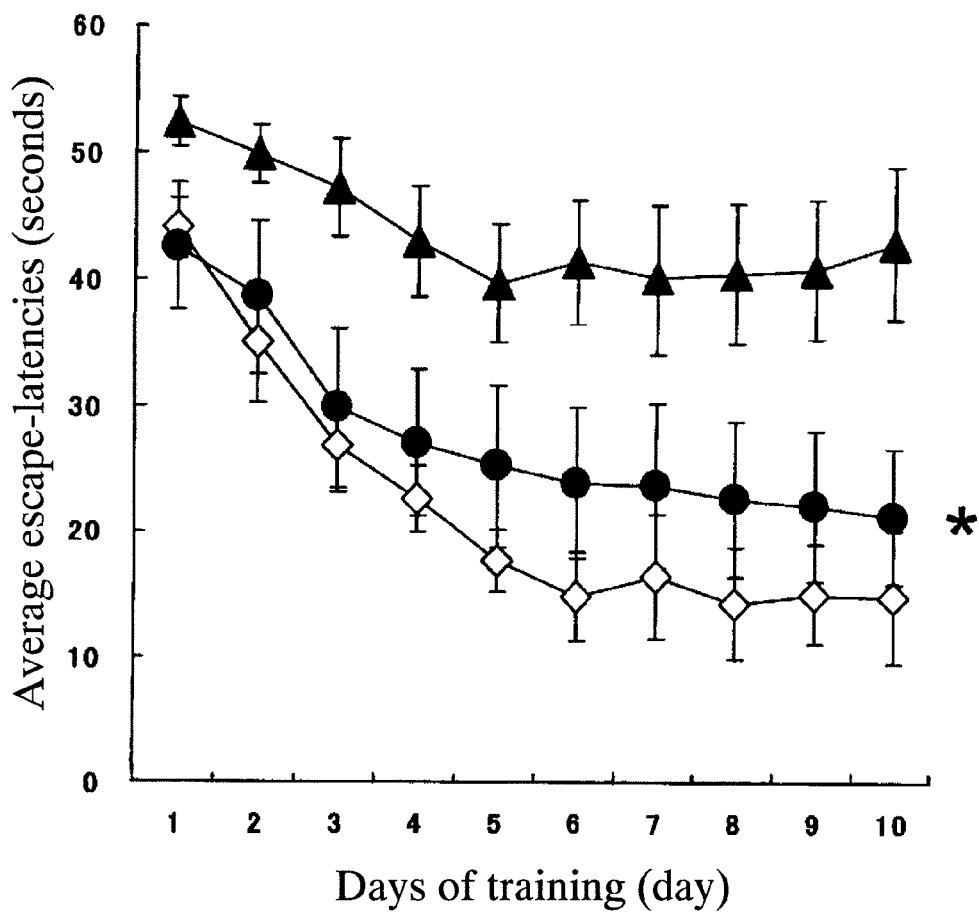
FIG. 3 is the antidepressant effect and the learning motivation-improving effect of continuous administration of (1S,3S)-MTCA in a behavioral scientific pharmacological test using a combination of open-space swimming and Morris water maze tests.

Further, transitions of average escape-latencies in the respective days up to Day 10 of administration are shown in FIG. 3. During the period, the effect that the time taken to reach the escape platform was decreased significantly was confirmed in the OS-(1S,3S)-MTCA-administered group, compared with the OS-Vehicle group (group of mice having depression) (FIG. 3). From the results, the antidepressant action and the learning motivation-improving action by the continuous administration of (1S,3S)-MTCA were confirmed.

EXAMPLE 4

PRODUCTION EXAMPLE 1

Pharmaceutical Tablet Comprising (1S,3S)-MTCA

Twenty grams of (1S,3S)-MTCA was mixed with 278.7 g of lactose and 1.3 g of magnesium stearate, and the mixture was made into tablets by a single punch tableting machine, whereby tablets with a diameter of 10 mm and a weight of 300 mg were produced.

PRODUCTION EXAMPLE 2

Granule Comprising (1S,3S)-MTCA

To 20 g of (1S,3S)-MTCA, 278.7 g of lactose and 1.3 g of magnesium stearate were added, and the mixture was compressed, ground, granulated, and sieved to obtain 20- to 50-mesh granules.

EXAMPLE 5

PRODUCTION EXAMPLE 3

Food and Beverage Comprising (1S,3S)-MTCA

In accordance with ingredients shown in Tables 3 to 8 below, a variety of foods comprising (1S,3S)-MTCA were produced by a method commonly used.

TABLE 3

Ice cream:

| (Composition) | (Weight by parts) |
|---|---|
| Fresh cream (45% fat) | 33.8 |
| Dried skim milk | 11.0 |
| Granulated sugar | 14.8 |
| Sugar-added egg yolk | 0.3 |
| Vanilla essence | 0.1 |
| Water | 39.98 |
| (1S,3S)-MTCA | 0.02 |
| Total weight | 100.0 |

TABLE 4

Juice:

| (Composition) | (Weight by parts) |
|---|---|
| Frozen concentrated unshu mikan juice | 5.0 |
| Fructose-glucose syrup | 11.0 |
| Citric acid | 0.2 |
| L-ascorbic acid | 0.02 |
| (1S,3S)-MTCA | 0.02 |
| Flavoring | 0.2 |
| Pigment | 0.1 |
| Water | 83.46 |
| Total weight | 100.0 |

TABLE 5

Lactic acid bacteria beverage:

| (Composition) | (Weight by parts) |
|---|---|
| Fermented milk with 21% milk solid | 14.76 |
| Fructose-glucose syrup | 13.31 |
| Pectin | 0.5 |
| Citric acid | 0.08 |
| Flavoring | 0.15 |
| Water | 71.18 |
| (1S,3S)-MTCA | 0.02 |
| Total weight | 100.0 |

TABLE 6

Yogurt:

| (Composition) | (Weight by parts) |
|---|---|
| Raw milk (3.4% fat) | 80.0 |
| Fresh cream (50% fat) | 8.0 |
| Dried skim milk | 1.5 |
| Water | 7.48 |
| Starter | 3.0 |
| (1S,3S)-MTCA | 0.02 |
| Total weight | 100.0 |

TABLE 7

Coffee beverage:

| (Composition) | (Weight by parts) |
|---|---|
| Granulated sugar | 8.0 |
| Dried skim milk | 5.0 |
| Caramel | 0.2 |

TABLE 7-continued

Coffee beverage:

| (Composition) | (Weight by parts) |
|---|---|
| Coffee extract | 2.0 |
| Flavoring | 0.1 |
| Polyglycerine fatty acid ester | 0.05 |
| Salt | 0.05 |
| Water | 84.58 |
| (1S,3S)-MTCA | 0.02 |
| Total weight | 100.0 |

TABLE 8

Alcoholic beverage:

| (Composition) | (Weight by parts) |
|---|---|
| 50% by volume ethanol | 32.0 |
| Sugar | 8.4 |
| Fruit juice | 2.4 |
| (1S,3S)-MTCA | 0.02 |
| Purified water | 57.18 |
| Total weight | 100.0 |

The invention claimed is:

1. A method for treating a disease or condition that can be ameliorated by inhibiting serotonin reuptake, comprising administering a pharmaceutical agent, food, or beverage comprising (1S,3S)-1-methyl-1,2,3,4-tetrahydro-β-carboline-3-carboxylic acid, wherein said disease or condition is selected from the group consisting of depression and decreased learning motivation and wherein (1S,3S)-1-methyl-1,2,3,4-tetrahydro-beta-carboline-3-carboxylic acid is the sole active ingredient.

2. The method according to claim 1, wherein the pharmaceutical agent, food, or beverage further comprises an additive acceptable as a pharmaceutical agent or food.

3. The method according to claim 1, wherein the (1S,3S)-1-methyl-1,2,3,4-tetrahydro-β-carboline-3-carboxylic acid is administered in an amount of 2 μg/kg to 50 mg/kg.

4. A method for inhibiting serotonin reuptake, comprising administering (1S,3S)-1-methyl-1,2,3,4-tetrahydro-β-carboline-3-carboxylic acid and wherein (1S,3S)-1-methyl-1,2,3,4-tetrahydro-beta-carboline-3-carboxylic acid is the sole active ingredient.

5. The method according to claim 4, wherein the (1S,3S)-1-methyl-1,2,3,4-tetrahydro-β-carboline-3-carboxylic acid is administered in an amount of 2 μg/kg to 50 mg/kg.

* * * * *